United States Patent [19]

Oka et al.

[11] Patent Number: 4,474,692

[45] Date of Patent: Oct. 2, 1984

[54] L-ALANYL-N-(INDAN-2-yl)GLYCINE, ITS ESTERS AND SALTS THEREOF

[75] Inventors: Yoshikazu Oka, Kawanishi; Kohei Nishikawa, Kyoto; Akio Miyake, Hirakata, all of Japan

[73] Assignee: Takeda Chemical Industries, Ltd., Osaka, Japan

[21] Appl. No.: 494,061

[22] Filed: May 12, 1983

Related U.S. Application Data

[62] Division of Ser. No. 312,639, Oct. 19, 1981.

[30] Foreign Application Priority Data

Oct. 31, 1980 [JP] Japan .............................. 55-154394
Apr. 28, 1981 [JP] Japan .............................. 56-64371

[51] Int. Cl.$^3$ ............................................ C07C 103/52
[52] U.S. Cl. ................................................ 260/112.5 R
[58] Field of Search ................................. 260/112.5 R

[56] References Cited

FOREIGN PATENT DOCUMENTS 2095682 10/1982 United Kingdom ......... 260/112.5 R

Primary Examiner—Delbert R. Phillips
Attorney, Agent, or Firm—Wegner & Bretschneider

[57] ABSTRACT

Useful intermediates for the preparation of hypotensives and inhibitors of angiotensin converting enzymes are L-alanyl-N-(indan-2-yl)glycine, its lower alkyl esters and the salts thereof.

6 Claims, No Drawings

L-ALANYL-N-(INDAN-2-yl)GLYCINE, ITS ESTERS AND SALTS THEREOF

This application is a division of Ser. No. 312,639, filed Oct. 19, 1981. Pending.

This invention relates to novel bicyclic compounds, which are useful as pharmaceuticals, and a process for producing the same.

As compounds having hypotensive effect due to inhibitory activity to angiotensin converting enzyme, there are known various amino acid derivatives [e.g. Japanese Patent Unexamined Publication (Kokai) Nos. 77-116457, 77-136117, 79-12372, 80-38382 and 80-81845, which correspond to U.S. Pat. Nos. 4,105,776, 4,053,651, British Unexamined Pub. No. 2000508, European Unexamined Pub. Nos. 9183 and 12401, respectively]. The compounds of the present invention are different from these known compounds in skeletal structure, and moreover have superior angiotensin converting enzyme inhibitory and hypotensive activities.

Thus, the present invention provides novel bicyclic compounds represented by the formula:

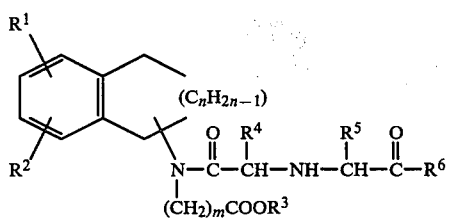

(I)

wherein $R^1$ and $R^2$ are the same or different and each represents hydrogen, hydroxyl or lower alkoxy; $R^3$ is hydrogen or lower alkyl; $R^4$ is hydrogen, lower alkyl, amino-lower-alkyl or acylamino-lower-alkyl; $R^5$ is hydrogen, lower alkyl or aralkyl which may be substituted; $R^6$ is hydroxyl, lower alkoxy, amino or lower alkylamino; and m and n each means 1 or 2, and salts thereof.

Referring to the above formula (I), the lower alkoxy group represented by $R^1$ or $R^2$ includes those containing about 1-4 carbon atoms, such as methoxy, ethoxy, propoxy, butoxy and isopropoxy. $R^1$ and $R^2$, when they are adjacent, may form a lower ($C_{1-4}$) alkylenedioxy, such as methylenedioxy or ethylenedioxy.

The lower alkyl group represented by $R^3$ includes those containing about 1-4 carbon atoms, such as methyl, ethyl, propyl, isopropyl, butyl, isobutyl, sec-butyl and tert-butyl.

The lower alkyl group represented by $R^4$ includes lower alkyl groups similar to those represented by $R^3$. The amino-lower-alkyl group represented by $R^4$ includes straight or branched ones containing about 1-4 carbon atoms, such as aminoethyl, 1-aminoethyl, 2-aminoethyl, 3-aminopropyl, 4-aminobutyl and 3-amino-2-methylpropyl. The acylamino-lower-alkyl group represented by $R^4$ includes those groups in which the amino group of the above-mentioned amino-lower-alkyl group is acylated with a carboxylic acid- or carbonate ester-derived acyl group. Said acyl group is, for example, $C_{2-4}$ alkanoyl (e.g. acetyl, propionyl), benzoyl, $C_{2-4}$ alkoxycarbonyl (e.g. ethoxycarbonyl) or benzyloxycarbonyl.

Referring to $R^5$, the lower alkyl group represented thereby includes lower alkyl groups similar to those represented by $R^3$. The aralkyl group represented by $R^5$ includes phenyl-lower ($C_{1-4}$)-alkyl containing about 7-10 carbon atoms, such as benzyl, phenethyl, 3-phenylpropyl, α-methylbenzyl, α-ethylbenzyl, α-methylphenethyl, β-methylphenethyl and β-ethylphenethyl. The phenyl moiety of said phenyl-lower-alkyl group may optionally have 1-3 substituents, such as halogen (e.g. fluorine, chlorine, bromine, iodine), $C_{1-4}$ alkyl (e.g. methyl, ethyl, propyl, butyl), $C_{1-4}$ alkoxy (e.g. methoxy, ethoxy, propoxy, isopropoxy, butoxy, methylenedioxy), amino, nitro or hydroxyl. Examples of such substituted phenyl-lower-alkyl group are 2-(4-chlorophenyl)ethyl, 2-(4-hydroxyphenyl)ethyl, 2-(4-methoxyphenyl)ethyl, 2-(3,4-dimethoxyphenyl)ethyl, 2-(3,4,5-trimethoxyphenyl)ethyl, 2-(3,4-methylenedioxyphenyl)ethyl, 2-(p-tolyl)ethyl, 3,4-dimethoxybenzyl, 3,4-methylenedioxybenzyl, 3,4,5-trimethoxybenzyl, 4-ethylbenzyl and 4-chlorobenzyl.

Referring to $R^6$, the lower alkoxy represented thereby includes lower alkoxy groups containing about 1-4 carbon atoms, such as methoxy, ethoxy, propoxy, isopropoxy, butoxy, isobutoxy, sec-butoxy, and tert-butoxy, and the lower alkylamino group includes mono- or di-lower ($C_{1-4}$)-alkylamino groups, such as methylamino, ethylamino, propylamino, butylamino, dimethylamino and diethylamino.

The salts of compounds (I) include pharmaceutically acceptable salts, for example, inorganic acid salts, such as hydrochloride, hydrobromide, sulfate, nitrate and phosphate; organic acid salts, such as acetate, tartrate, citrate, fumarate, maleate, toluenesulfonate and methanesulfonate; metal salts, such as sodium, potassium, calcium and aluminum salts; and salts with bases, such as triethylamine, guanidine, ammonium, hydrazine, quinine and cinchonine salts.

In the above-mentioned compounds (I), preferred embodiments are those of the formula (I) wherein $R^1$ and $R^2$ independently represent hydrogen, hydroxyl or $C_{1-4}$ alkoxy, or $R^1$ and $R^2$ jointly form $C_{1-4}$ alkylenedioxy; $R^3$ is hydrogen or $C_{1-4}$ alkyl; $R^4$ is hydrogen, $C_{1-4}$ alkyl or amino$C_{1-4}$ alkyl which is unsubstituted or substituted by acyl of the class consisting of $C_{2-4}$ alkanoyl, benzoyl, $C_{2-4}$ alkoxycarbonyl or benzyloxycarbonyl; $R^5$ is hydrogen, $C_{1-4}$ alkyl or phenyl-$C_{1-4}$ alkyl which is unsubstituted or substituted by 1 to 3 members of halogen, $C_{1-4}$ alkyl, $C_{1-4}$ alkoxy, amino, nitro and hydroxyl, $R^6$ is hydroxyl, $C_{1-4}$ alkoxy, amino or mono- or di-$C_{1-4}$ alkylamino; and m and n each means 1 or 2, and pharmaceutically acceptable salts thereof.

Among the compounds (I), further preferred are compounds wherein $R^1$ and $R^2$ are each hydrogen, $R^3$ is hydrogen, $R^4$ is lower ($C_{1-4}$) alkyl or amino-lower($C_{1-4}$)alkyl, $R^5$ is phenethyl, $R^6$ is lower($C_{1-4}$) alkoxy or hydroxyl, and m and n are each 1, or compounds of the formula:

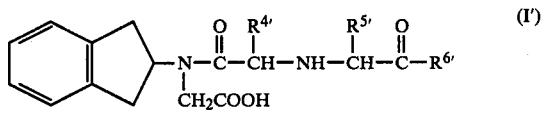

(I')

wherein $R^{4'}$ is hydrogen or $C_{1-4}$ alkyl, $R^{5'}$ is hydrogen, $C_{1-4}$ alkyl or phenyl-$C_{1-4}$ alkyl, and $R^{6'}$ is hydroxyl or $C_{1-4}$ alkoxy, and their pharmaceutically acceptable salts.

Referring to the above formula (I'), the groups in $R^{4'}$, $R^{5'}$ and $R^{6'}$ correspond to those of $R^4$, $R^5$ and $R^6$ respectively.

A preferable specific embodiment in the present invention is N-(1-ethoxycarbonyl-3-phenylpropyl)-L-alanyl-N-(indan-2-yl)glycine and its pharmaceutically acceptable salts.

The compounds (I) of the present invention can be produced, for example, by subjecting a compound of the formula:

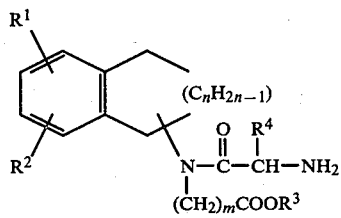

wherein the symbols are each as above defined, and a compound of the formula:

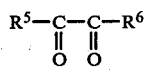

wherein $R^5$ and $R^6$ are as above defined, to condensation under reductive conditions.

Said reductive conditions include those reaction conditions used in catalytic reduction using as a catalyst such as metal as platinum, palladium, Raney nickel or rhodium or a mixture thereof with an appropriate carrier; reduction with a metal hydride compound such as lithium aluminum hydride, lithium borohydride, lithium cyanoborohydride, sodium borohydride or sodium cyanoborohydride; reduction with metallic sodium or metallic magnesium and an alcohol; reduction with such a metal as iron or zinc and such an acid as hydrochloric acid or acetic acid; electrolytic reduction and reduction with a reducing enzyme. The above reaction is usually carried out in the presence of water or an organic solvent (e.g. methanol, ethanol, ethyl ether, dioxane, methylene chloride, chloroform, benzene, toluene, acetic acid, dimethylformamide, dimethylacetamide). The reaction temperature depends on the means of reduction employed, but generally temperatures ranging from $-20°$ C. to $+100°$ C. are preferred. The reaction can proceed in a satisfactory manner at ordinary pressure, but the reaction may also be carried out under pressure or under reduced pressure according to circumstances.

Those compounds (I) wherein $R^3$ is hydrogen or/and $R^6$ is hydroxyl can also be produced by hydrolysis of the corresponding ester compounds or by catalytic reduction of the corresponding benzyl esters.

The compound (I) can further be produced by subjecting a compound of the formula:

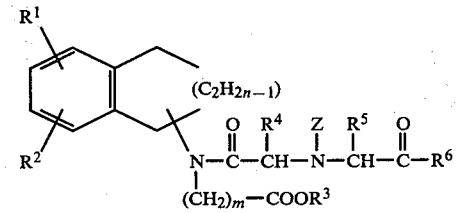

wherein Z is a protective group removable by hydrolysis or catalytic reduction and the other symbols are each as above defined, to hydrolysis or catalytic reduction.

The protective group represented by Z in formula (IV) and removable by hydrolysis includes all sorts of acyl groups and trityl. In particular, such groups as benzyloxycarbonyl, tert-butoxy carbonyl, trifluoroacetyl and trityl are advantageous for a reaction under relatively mild conditions. The protective group represented by Z and removable by catalytic reduction includes benzyl, diphenylmethyl and benzyloxycarbonyl, among others. The hydrolysis reaction in this method is carried out in water or an organic solvent such as methanol, ethanol, dioxane, pyridine, acetic acid, acetone or methylene chloride, or a mixture thereof. For accelerating the reaction, an acid (e.g. hydrochloric, hydrobromic, hydroiodic, hydrofluoric, sulfuric, methanesulfonic, p-toluenesulfonic or trifluoroacetic acid) or a base (e.g. sodium hydroxide, potassium hydroxide, potassium carbonate, sodium hydrogen carbonate, sodium acetate, triethylamine) may be added to the reaction system. The reaction temperature is usually in the range of about $-10°$ C. to $+150°$ C. The catalytic reduction in this method is carried out in water or an organic solvent such as methanol, ethanol, dioxane or tetrahydrofuran, or a mixture thereof, in the presence of an appropriate catalyst such as platinum or palladium-carbon. This reaction is carried out at ordinary pressure or under pressure up to about 150 kg/cm² and at ordinary temperature or a temperature up to 150° C. Generally, the reaction can proceed sufficiently smoothly at ordinary temperature and at ordinary pressure.

The compounds (I) can also be produced by reacting a compound (II) with a compound of the formula:

wherein $R^5$ and $R^6$ are each as above defined and X is halogen or a group of the formula $R^7SO_2-O-$ in which $R^7$ is lower alkyl, phenyl or p-tolyl. The reaction is carried out by maintaining both the reactants in an appropriate solvent at a temperature within the range of about $-10°$ C. to about $+150°$ C. For accelerating the reaction, such a base as potassium carbonate, sodium hydroxide, sodium hydrogen carbonate, pyridine or triethylamine may be made to coexist in the reaction system as a deacidifying agent.

The object compounds (I) of the present invention produced in this way can be isolated from the reaction mixture by usual means of separation and purification, such as extraction, concentration, neutralization, filtration, recrystallization, column chromatography and/or thin layer chromatography.

Depending on the presence or absence of the substituents represented by $R^4$ and $R^5$, there may exist two to eight steric isomers of a compound (I). These individual isomers and mixtures thereof naturally fall within the scope of the present invention. Such isomers, if desired, can be prepared individually. For example, a single optical isomer of (I) can be obtained by carrying out the above reaction using a single isomer of the starting compound (II) or (IV). When the product is a mixture of two or more isomers, they can be separated into individual isomers by a usual separation technique, such as salt formation using an optically active acid (e.g. camphorsulfonic, tartaric or dibenzoyltartaric acid) or an optically active base (e.g. cinchonine, cinchonidine, quinine, quinidine, alphamethylbenzylamine, dehydroabietylamine), a variety of chromatographic techniques or fractional crystallization. For those compounds (I) wherein $R^4$ and $R^5$ are each other than hydrogen, the isomers respectively having an S configuration generally have more preferable physiological activities as compared with the corresponding compounds having an R configuration.

The compounds of the present invention, i.e., the bicyclic compounds represented by formula (I) and pharmaceutically acceptable salts thereof, exhibit inhibitory activities on angiotensin converting enzyme, bradykinin decomposing enzyme (kininase) and enkephalinase in animals, in particular, mammals (e.g. human, dog, cat, rabbit, guinea pig, rat) and therefore are useful as drugs for diagnosis, prevention or treatment of hypertension and as analgesic and analgesic-activity-potentiating agents. The compounds of the present invention are of low toxicity, well absorbed even on oral administration and highly stable. Therefore, when they are used as the above-mentioned drugs, they can safely be administered orally or parenterally, per se or in admixture with suitable pharmaceutically acceptable carriers, excipients or diluents in various pharmaceutical formulations such as powders, granules, tablets, capsules, injectable solutions, etc. While the dosage level generally varies depending upon the conditions of the diseases to be treated as well as the administration route used, for example, in the treatment of hypertension in adult human, the compounds may be administered orally at a single dose of about 0.02–20 mg/kg, preferably about 0.2–2 mg/kg, or intravenously at about 0.002–0.2 mg/kg, preferably about 0.02–0.2 mg/kg, about 2 to 5 times per day according to the conditions.

The starting compounds (II) of this invention can easily be prepared, for example, by the process shown by the following reaction scheme:

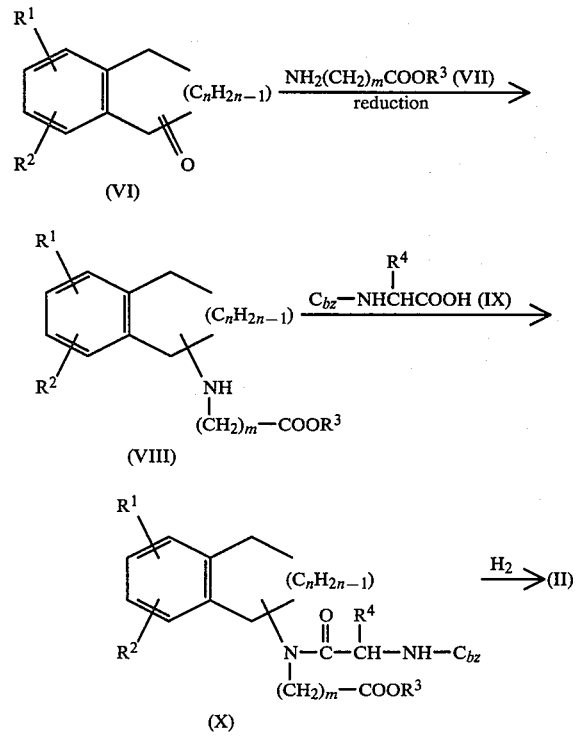

In the above formulas, $R^1$, $R^2$, $R^3$, $R^4$, m and n are as above defined, and $C_{bz}$ is benzyloxycarbonyl.

The process for preparing (II) as shown by the above reaction scheme is now illustrated in more detail. Firstly, in the step (VI)→(VIII), (VI) and (VII) are reacted in an appropriate solvent to yield a Schiff base, which is then subjected to reduction. An organic solvent such as methanol, ethanol, dioxane, methylene chloride, chloroform, benzene or toluene is used as the solvent, and the reaction is conducted generally at a temperature within the range of about $-10°$ C. to $+150°$ C. For advantageous progress of the reaction, a catalyst, such as sulfuric acid or p-toluenesulfonic acid, or a dehydrating agent, such as anhydrous sodium sulfate, anhydrous magnesium sulfate or calcium chloride, may be added to the reaction mixture. It is also possible to make the reaction proceed advantageously by using a water separating device (trap). The Schiff base obtained is, either in the form of a reaction mixture or after isolation in a usual manner, again added to a solvent and subjected to reduction. The means of reduction include catalytic reduction using platinum or palladium-carbon, for instance, as a catalyst, and a method using such a reducing agent as sodium borohydride or sodium cyanoborohydride.

It is also possible to make the Schiff base formation and reduction proceed simultaneously be allowing such a reducing agent to coexist in the reaction mixture of (VI) and (VII) from the beginning. In the step (VIII)→(X), (VIII) is reacted with (IX) or a carboxyl-derived functional derivative thereof. The carboxyl-derived functional derivative of compound (IX) includes among others acid halides, such as acid chloride and acid bromide; acid anhydrides obtainable by removing one mole of water from two moles of (IX); mixed anhydrides formed by substitution of the hydrogen atom of the carboxyl group in (IX) by ethoxycarbonyl, isobutyloxycarbonyl, benzyloxycarbonyl, etc.; and reactive esters of (IX) derived from 1-hydroxybenzotriazole, N-hydroxyphthalimide, N-hydroxysuccinimide, etc. Generally, the reaction is carried out in an appropriate solvent, which may be of any kind so long as it does not disturb the reaction. When (IX) is used as it is without converting it to a functional derivative, the reaction is preferably carried out in the presence of a dehydrating agent such as dicyclohexylcarbodiimide or carbonyldiimidazole. When an acid halide is used as the functional derivative, the reaction may also be carried out in the presence of a base such as pyridine, picoline, triethylamine, sodium hydroxide, sodium hydrogen carbonate or sodium carbonate. Generally, the reaction temperature is within the range of about $-20°$ C. to about $+150°$ C. In most cases, however, the reaction can proceed in a satisfactory manner at ordinary temperature. The step (X)→(II) consists in removal of the N-protecting group by catalytic reduction. The catalytic reduction is carried out in water or an organic solvent, such as methanol, ethanol, dioxane, tetrahydrofuran or acetic acid, or a mixture thereof, in the presence of an appropriate catalyst, such as platinum, palladium-carbon or Raney nickel. This reaction is carried out at ordinary pressure to about 150 kg/cm² and at ordinary temperature to 150° C. Generally, the reaction can proceed in a satisfactory manner at ordinary temperature.

The invention will be further illustrated in more detail by the following reference examples, embodiment examples, test examples and dosage form examples, which, however, are by no means limitative of the present invention.

INTERMEDIATE EXAMPLE 1

Glycine ethyl ester hydrochloride (20 g) is dissolved in a solution of 10 g of 2-indanone in 200 ml of methanol, and then 5.0 g of sodium cyanoborohydride is added portionwise to the solution with ice cooling and stirring. After stirring at room temperature for 2 hours, the reaction mixture is poured into 500 ml of ice water, and the whole mixture is made alkaline with sodium hydrogen carbonate and extracted with 300 ml of ethyl acetate. The extract is washed with water and dried, the ethyl acetate is distilled off under reduced pressure, 10 ml of 20% ethanolic hydrochloric acid and 200 ml of ethyl ether are added to the residue, and the mixture is allowed to stand at room temperature. The resulting crystalline precipitate is collected by filtration and dried to give 11 g of N-(indan-2-yl)glycine ethyl ester hydrochloride as colorless needles melting at 164°–167° C.

INTERMEDIATE EXAMPLE 2

To a solution of 5 g of 2-indanone in 150 ml of methanol is added 15 g of glycine benzyl ester paratoluenesulfonate, and then 5 g of sodium cyanoborohydride is added portionwise with ice cooling and stirring. Thereafter, the mixture is treated in the same manner as in Intermediate Example 1 to give 6.5 g of N-(indan-2-yl)glycine benzyl ester hydrochloride as colorless prisms melting at 186°–189° C.

INTERMEDIATE EXAMPLE 3

2-Indanone (40 g) is dissolved in 300 ml of methanol, 78 g of glycine tert-butyl ester phosphite and 150 g of water are added, and then 23 g of sodium cyanoborohydride is added over 15 minutes with ice cooling and stirring. The resulting mixture is further stirred at room temperature for 4 hours. To the reaction mixture, 400 ml of 20% phosphoric acid is added portionwise over an hour, 200 ml of water is then added, the mixture is stirred for 30 minutes and then extracted with 800 ml of ethyl ether, and the aqueous layer is adjusted to pH 10 with 20% sodium hydroxide and extracted with 4 portions (500 ml in total) of chloroform. The extract is dried over anhydrous sodium sulfate and then distilled under reduced pressure. 50 ml of ethanol and then 150 ml of water are added to the oil obtained, and the mixture is cooled. The crystalline precipitate is collected by filtration and recrystallized twice from aqueous ethanol to give 47 g of (indan-2-yl)glycine tert-butyl ester as colorless prisms melting at 54°–55° C.

INTERMEDIATE EXAMPLE 4

A solution of 22.3 g of N-carbobenzoxy-L-alanine and 14 ml of triethylamine in 200 ml of tetrahydrofuran is cooled to −10° C., and 13.1 ml of isobutyl chlorocarbonate is added dropwise in portions with stirring. After stirring for 30 minutes, a solution of 24.1 g of N-(indan-2-yl)glycine ethyl ester hydrochloride and 14 ml of triethylamine in 200 ml of chloroform is added dropwise at −10° C. to −5° C. After standing overnight at room temperature, the reaction mixture is washed in sequence with water, aqueous sodium hydrogen carbonate, 10% hydrochloric acid and water, and dried over anhydrous sodium sulfate. The solvent is distilled off under reduced pressure, the residue is dissolved in 100 ml of methanol, 75 ml of 2N sodium hydroxide is added, and the mixture is stirred at room temperature for 2 hours. Then, the mixture is made acidic with 10% hydrochloric acid to separate the resulting oil, which is extracted with 500 ml of ethyl acetate. The extract washed with water and dried, and the solvent is distilled off under reduced pressure to give 25 g of N-carbobenzoxy-L-alanyl-N-(indan-2-yl)glycine as an oil. This is dissolved in 50% ethanol and subjected to catalytic reduction in the presence of 4 g of 10% palladium-carbon. When the hydrogen absorption has ceased, the catalyst is filtered off, and the filtrate is concentrated under reduced pressure. Addition of 50 ml of methanol to the residue yields 11 g of L-alanyl-N-(indan-2-yl)glycine as colorless needles melting at 180°–182° C.

INTERMEDIATE EXAMPLE 5

N-Carbobenzoxy-L-alanine (21.8 g) and 12.3 ml of triethylamine are dissolved in 200 ml of tetrahydrofuran, and 8.5 g of ethyl chlorocarbonate is added dropwise at −15° C. with stirring. After the dropping, stirring is continued for 15 minutes, and then a solution of 22 g of (indan-2-yl)glycine tert-butyl ester in 100 ml of chloroform is added dropwise at −10° C. or below. After stirring at room temperature for an hour, the reaction mixture is poured into 500 ml of water, and the chloroform layer is separated and the chloroform is distilled off. The residue is dissolved in 300 ml of ethyl acetate, the solution is washed with two 50-ml portions of 1N aqueous sodium hydroxide, one 50-ml portion of water, two 50-ml portions of 20% aqueous phosphoric acid and one 50-ml portion of water, in that order, and then dried over anhydrous magnesium sulfate, and the solvent is distilled off to give 35 g of N-carbobenzoxy-L-alanyl-N-(indan-2-yl)glycine tert-butyl ester as an oil. This is dissolved in 300 ml of methanol and, after addition of 7 g of oxalic acid and 3.5 g of 10% palladium-carbon (containing 50% water), is subjected to catalytic reduction at ordinary temperature and ordinary pressure. After the reaction, the catalyst is filtered off, the filtrate is distilled off under reduced pressure, and 500 ml of ethanol is added to the residue. On cooling, a precipitate forms, which is collected by filtration and dried to give 21.8 g of L-alanyl-N-(indan-2-yl)glycine tert-butyl ester oxalate melting at 138°–141° C.

$[\alpha]_D^{22} + 20.4°$ (c=1, methanol)

INTERMEDIATE EXAMPLE 6

N-(Indan-2-yl)glycine benzyl ester hydrochloride (6 g) is added to a mixture of 300 ml of ethyl acetate and 200 ml of 5% aqueous potassium carbonate, followed by vigorous stirring. To the resulting solution is added dropwise 6 ml of chloroacetyl chloride over 30 minutes with ice cooling. Thereafter, stirring is continued for an hour. The ethyl acetate layer is then separated, washed with water and dried over anhydrous magnesium sulfate, and the solvent is distilled off under reduced pressure. Addition of ether to the residue gives 6 g of N-chloroacetyl-N-(indan-2-yl)glycine benzyl ester as colorless scales melting at 99.5°–100.5° C.

INTERMEDIATE EXAMPLE 7

N-Chloroacetyl-N-(indan-2-yl)glycine benzyl ester (3 g) and 2 g of N-benzylglycine ethyl ester are dissolved in 50 ml of methyl ether ketone, 10 g of potassium carbonate is added, and the mixture is refluxed for 24 hours with stirring. After cooling, the insoluble matter is filtered off, and the filtrate is distilled under reduced pressure to give an oil. This is purified by silica gel column chromatography to give 3 g of N-ethoxycarbonylmethyl-N-benzylglycyl-N-(indan-2-yl)glycine benzyl ester as an oil.

Infrared (IR) Absorption Spectrum $\nu_{max}^{Neat}$ cm$^{-1}$: 1730, 1640.

INTERMEDIATE EXAMPLE 8

By reacting 7 g of N-(indan-2-yl)glycine tert-butyl ester with 8.5 g of N-(carbobenzoxy)-L-leucine and treating the reaction mixture as in Reference Example 5, there is obtained 3.5 g of L-leucyl-N-(indan-2-yl)glycine tert-butyl ester as colorless amorphous powder.

INTERMEDIATE EXAMPLE 9

By reacting 8.2 g of N-(indan-2-yl)glycine tert-butyl ester with 13 g of $N^\alpha$-tert-butoxycarbonyl-$N^\epsilon$-carbobenzoxy-L-lysine as in Reference Example 5, there is obtained 14 g of $N^\alpha$-tert-butoxycarbonyl-$N^\epsilon$-carbobenzoxy-L-lysyl-N-(indan-2-yl)glycine tert-butyl ester as a colorless oil.

NMR(CDCl$_3$) δ: 1.40, 1.45(18H), 5.05(2H), 7.0–7.3(9H).

IR Spectrum $\nu_{max}^{neat}$ cm$^{-1}$: 1700, 1640.

$[\alpha]_D^{24} -14.3°$ (c=0.9, methanol).

INTERMEDIATE EXAMPLE 10

$N^\alpha$-tert-Butoxycarbonyl-$N^\epsilon$-carbobenzoxy-L-lysyl-N-(indan-2-yl)glycine tert-butyl ester (5 g) obtained by the procedure of Reference Example 9 is dissolved in 100 ml of 1N solution of hydrogen chloride in ethyl acetate, and the solution is allowed to stand at room temperature for 6 hours. On adding 500 ml of petroleum ether to the reaction mixture, an oily substance separates, which is isolated. The solution layer is concentrated under reduced pressure and again subjected to a similar treatment with hydrogen chloride. The oil fractions obtained are combined, dissolved in 100 ml of ethyl acetate, and washed with 100 ml of 1N aqueous sodium hydroxide and with water. The organic layer is dried over anhydrous magnesium sulfate and, after addition of 1 g of oxalic acid, the solvent is distilled off under reduced pressure. Addition of a mixture of ether and petroleum ether to the residue yields 2.4 g of $N^\epsilon$-carbobenzoxy-L-lysyl-N-(indan-2-yl)glycine tert-butyl ester oxalate as colorless powder.

Elemental analysis for C$_{29}$H$_{39}$N$_3$O$_5$·C$_2$H$_2$O$_4$·H$_2$O: Calcd.: C, 60.28; H, 7.02; N, 6.80. Found: C, 59.83; H, 7.01; N, 6.41.

$[\alpha]_D^{23.5} +17.5°$ (c=1, methanol).

INTERMEDIATE EXAMPLE 11

In a solution of 13 g of 2-indanone in 100 ml of methanol, there is dissolved 13 g of β-alanine ethyl ester hydrochloride, and, with ice cooling and stirring, 6.5 g of sodium cyanoborohydride is added portionwise. After standing at room temperature overnight, the mixture is poured into 500 ml of ice water, made alkaline with sodium hydrogen carbonate and extracted with 200 ml of chloroform. The extract is washed with water, and dried, followed by distilling off chloroform under reduced pressure. To the residue, 10 ml of 20% ethanolic hydrochloric acid and 50 ml of ethyl ether are added successively, and the mixture is allowed to stand at room temperature. The resulting precipitate is collected by filtration and dried to give 10 g of N-(indan-2-yl)-β-alanine ethyl ester hydrochloride as colorless scales melting at 150°–151° C.

INTERMEDIATE EXAMPLE 12

By reacting 7 g of N-(indan-2-yl)-β-alanine ethyl ester hydrochloride with 7 g of N-carbobenzoxy-L-alanine and treating the reaction mixture as in Reference Example 4, there is obtained 5 g of L-alanyl-N-(indan-2-yl)-β-alanine. Melting point 205°–206° C.

$[\alpha]_D^{23.5} +16°$ (c=0.8, 1N HCl).

INTERMEDIATE EXAMPLE 13

In a solution of 20 g of 1,2,3,4-tetrahydro-2-naphthalenone in 200 ml of methanol, there is dissolved 23 g of glycine ethyl ester hydrochloride, and 9.0 g of sodium cyanoborohydride is added portionwise with ice cooling and stirring. After stirring at room temperature for 2 hours, the reaction mixture is poured into 500 ml of ice water, and the whole mixture is made alkaline with sodium hydrogen carbonate and extracted with 500 ml of ethyl acetate. The extract is washed with water and dried, the ethyl acetate is distilled off under reduced pressure, 10 ml of 20% ethanolic hydrochloric acid and 200 ml of ethyl ether are added to the residue, and the mixture is allowed to stand at room temperature. The crystalline precipitate is collected by filtration and dried to give 25 g of N-(1,2,3,4-tetrahydronaphthalen-2-yl)glycine ethyl ester hydrochloride as colorless needles melting at 198°–200° C.

REFERENCE EXAMPLE 14

By reacting 13.5 g of N-(1,2,3,4-tetrahydronaphthalen-2-yl)glycine ethyl ester hydrochloride with 11.6 g of N-carbobenzoxy-L-alanine and treating the reaction mixture as in Reference Example 4, there is obtained 7.5 g of L-alanyl-N-(1,2,3,4-tetrahydronaphthalen-2-yl)glycine as colorless amorphous powder.

IR spectrum $\nu_{max}^{Nujol}$ cm$^{-1}$: 1720, 1640.

REFERENCE EXAMPLE 15

By reacting 13 g of (indan-1-yl)glycine ethyl ester hydrochloride with 11.6 g of N-carbobenzoxy-L-alanine and treating the reaction mixture as in Reference Example 4, there is obtained 8.0 g of L-alanyl-N-(indan-1-yl)glycine as colorless amorphous powder.

IR spectrum $\nu_{max}^{Nujol}$ cm$^{-1}$: 1730, 1640.

REFERENCE EXAMPLE 16

By reacting 10 g of (5-benzyloxyindan-1-yl)glycine ethyl ester with 8 g of N-carbobenzoxy-L-alanine and treating the reaction mixture as in Reference Example 4, there is obtained 5.2 g of L-alanyl-N-(5-hydroxyindan-1-yl)glycine as colorless amorphous powder.

REFERENCE EXAMPLE 17

5,6-Dimethoxy-1-indamine hydrochloride (11 g) is suspended in 200 ml of methyl ethyl ketone, then 6.9 g of potassium carbonate, 2.0 g of potassium iodide and 8.2 g of tert-butyl chlorocarbonate are added, and the mixture is refluxed for 8 hours. The reaction mixture is poured into 500 ml of water and extracted with 200 ml of ethyl acetate, the extract is washed with water and dried, and the ethyl acetate is distilled off under reduced pressure. The residue is subjected to silica gel column chromatography and eluted with hexane-acetone (7:3) to give 6.0 g of N-(5,6-dimethoxyindan-1-yl)glycine tert-butyl ester as an oil. This is dissolved in 50 ml of ethyl ether, 2.0 g of oxalic acid is added, and the mixture is allowed to stand at room temperature. There is thus obtained 7.3 g of N-(5,6-dimethoxyindan-1-yl)glycine tert-butyl ester oxalate as colorless needles melting at 158°–160° C.

REFERENCE EXAMPLE 18

By reacting 7 g of N-(5,6-dimethoxyindan-1-yl)glycine tert-butyl ester oxalate with 4.8 g of N-carbobenzoxy-L-alanine and treating the reaction mixture as in Reference Example 5, there is obtained 4 g of L-alanyl-N-(5,6-dimethoxy-indan-1-yl)glycine tert-butyl ester oxalate as colorless amorphous powder.

REFERENCE EXAMPLE 19

A mixture of 143 g of ethyl 3-phenylpropionate, 234 g of ethyl oxalate and 154 ml of 28% sodium ethoxide solution in ethanol is heated on a water bath at a bath temperature of 60°–70° C. for 1.5 hours, while distilling off the ethanol under reduced pressure. To the resulting red syrupy residue is added 1.3 liters of 15 v/v % sulfuric acid. The mixture is boiled under reflux with stirring for 15 hours, and the oil layer is separated, neutralized with 10% sodium hydroxide and extracted with ethyl acetate. The aqueous layer is made acidic with diluted sulfuric acid. The resulting oil is extracted with ethyl acetate, washed with water and dried. Removal of the ethyl acetate by distillation under reduced pressure gives 130 g of 2-oxo-4-phenylbutyric acic as an oil.

REFERENCE EXAMPLE 20

2-Oxo-4-phenylbutyric acid (130 g) is added to a mixture of 650 ml of ethanol and 13 ml of concentrated sulfuric acid, and the whole mixture is refluxed for 5 hours. The reaction mixture is concentrated to approximately half the original volume, and then diluted with 500 ml of water. The resulting oil is collected and, the aqueous layer is extracted with ethyl acetate. The extract and the oil are combined and dried, and the solvent is distilled off under reduced pressure. The residue is distilled under reduced pressure to give 113 g of ethyl 2-oxo-4-phenylbutyrate as a colorless oil boiling at 135°–141° C./3 mmHg.

REFERENCE EXAMPLES 21–27

Compounds shown in Table 1 can be prepared from the respectively corresponding starting compounds by a similar manner to Reference Examples 19 and 20.

TABLE 1

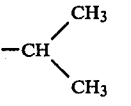

| Ref. Ex. No. | R' | R'' | Boiling Point |
|---|---|---|---|
| 21 | H | CH$_3$ | 108–112° C./0.5 mmHg |
| 22 | H | —(CH$_2$)$_2$CH$_3$ | 105–118° C./1 mmHg |
| 23 | H | —CH(CH$_3$)$_2$ | 132–135° C./3 mmHg |
| 24 | H | —(CH$_2$)$_3$CH$_3$ | 145–150° C./4 mmHg |
| 25 | H | —CH$_2$—CH(CH$_3$)$_2$ | 120–132° C./0.5 mmHg |
| 26 | Cl | —CH$_2$CH$_3$ | 125–135° C./1 mmHg |

TABLE 1-continued

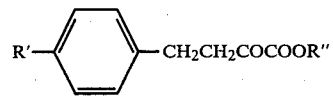

| Ref. Ex. No. | R' | R'' | Boiling Point |
|---|---|---|---|
| 27 | CH$_3$ | —CH$_2$CH$_3$ | 120–130° C./1 mmHg |

REFERENCE EXAMPLE 28

Piperidine (7.5 ml) is added to a solution of 99.6 g of veratrum aldehyde and 124.8 g of malonic acid in 240 ml of pyridine, and the mixture is heated at 80°–85° C. for an hour and further at 110°–115° C. for 3 hours. After cooling, the reaction mixture is poured into a large amount of water, and the resulting crystalline precipitate is collected by filtration. The crystals are dissolved in diluted aqueous sodium hydroxide. The solution is made acidic with hydrochloric acid to give 70 g of 3,4-dimethoxycinnamic acid as needles melting at 182°–183° C. 35 g of these crystals are dissolved in 500 ml of ethanol, and the solution is saturated with gaseous hydrogen chloride and allowed to stand at room temperature overnight. The crystals obtained by distilling off the ethanol are dissolved in ethyl acetate. The solution is washed with diluted aqueous sodium hydrogen carbonate and with water, and dried. The crystals obtained by distilling off the ethyl acetate are recrystallized from ethanol to give 65 g of ethyl 3,4-dimethoxycinnamate as scales melting at 53°–55° C. 34 g of these crystals are dissolved in 300 ml of ethanol, 10 g of 5% palladium-carbon is added to the solution, and the mixture is shaken in a hydrogen atmosphere at room temperature. After 3 hours, the catalyst is filtered off, and the filtrate is concentrated to give 34 g of ethyl 3,4-dimethoxyphenylpropionate as an oil. A solution of 34.1 g of this oil in 43 g of diethyl oxalate is added to a sodium ethoxide solution (prepared from 3.8 g of metallic sodium and 150 ml of ethanol) at 60° C. with stirring. After completion of the addition, stirring is continued at 70°–75° C. for further 3 hours. The ethanol is distilled off under reduced pressure, 200 ml of water is added to the residue, and the mixture is washed with ethyl acetate. The aqueous layer is made acidic with hydrochloric acid and then extracted with ethyl acetate. The ethyl acetate layer is washed with water, dried and concentrated to give 27 g of ethyl 2-oxo-3-ethoxycarbonyl-4-(3,4-dimethoxyphenyl)butyrate as an oil. 26 g of this oil is dissolved in a mixture of 80 ml of dimethyl sulfoxide and 8 ml of water. To the solution is added 6.3 g of sodium chloride, and the mixture is stirred at 120° C. for 2 hours. After cooling, a large amount of water is added, and the mixture is extracted with ethyl acetate. The extract is washed with water, dried and concentrated to give crystals. Recrystallization from ether yields 15 g of ethyl 2-oxo-4-(3,4-dimethoxyphenyl)butyrate and pillars melting at 85°–87° C.

REFERENCE EXAMPLE 29

Proceeding as in Reference Example 28, there is obtained ethyl 4-(p-benzyloxyphenyl)-2-oxobutyrate as a yellow oil from the corresponding starting material.

NMR Spectrum (CDCl$_3$) δ: 1.3(t,3H), 2.7–3.3(m,4H), 4.3 (q,2H), 5.0(s,2H), 6.7–7.4(m,9H).

In the above NMR data, s means a singlet, d a doublet, t a triplet, q a quartet, m a multiplet, and Ph a phenyl group. (Hereinafter the same shall apply.)

REFERENCE EXAMPLE 30

2-Oxo-4-phenylbutyric acid (9 g) is dissolved in 100 ml of benzene, and 10 g of phosphorus pentachloride is added thereto portionwise with ice cooling. After stirring at room temperature for an hour, a solution of 10 g of butylamine in 20 ml of tetrahydrofuran is added dropwise to the benzene solution. The reaction mixture is stirred at room temperature for 30 minutes and poured into 100 ml of ice water. The mixture is extracted with ethyl acetate, the extract is washed with water and dried, and the ethyl acetate is distilled off under reduced pressure. The residue is subjected to silica gel column chromatography by the use of hexane-acetone (7:3) as the eluent to give 6.0 g of N-butyl-2-oxo-4-phenylbutylamide as a slightly yellow oil.

NMR spectrum (CDCl$_3$) δ: 0.90(3H,m,CH$_3$), 1.20–1.50(4H, m), 2.70–3.40(5H,m), 7.20(5H,s,Ph).

EXAMPLE 1

To a solution of 1.0 g of L-alanyl-N-(indan-2-yl)glycine and 6.0 g of ethyl 2-oxo-4-phenylbutyrate in 200 ml of ethanol, there is added 8 g of molecular sieve, and the mixture is stirred at room temperature for an hour. Then, 1.0 g of sodium cyanoborohydride is added. After standing overnight, the reaction mixture is concentrated under reduced pressure, the residue is adjusted to pH 9.0 with 10% sodium hydroxide, and the insoluble matter is removed by extraction with ethyl ether. The aqueous solution is adjusted to pH 4 with 10% hydrochloric acid and extracted with two 200-ml portions of ethyl acetate. The extract is washed with water and dried over sodium sulfate, and the solvent is distilled off under reduced pressure. The residue is dissolved in 2 ml of 20% ethanolic hydrochloric acid, 100 ml of ethyl ether is then added, and the mixture is allowed to stand at room temperature to give 0.4 g of N-(1-ethoxycarbonyl-3-phenylpropyl)-L-alanyl-N-(indan-2-yl)glycine hydrochloride melting at 168°–170° C.

EXAMPLE 2

L-Alanyl-N-(indan-2-yl)glycine tert-butyl ester oxalate (21 g) is dissolved in 200 ml of ethanol. To the solution 4.1 g of sodium acetate, 10 ml of acetic acid, 25 g of ethyl 2-oxo-4-phenylbutyrate and 25 g of molecular sieve 3A are added in sequence. Thereafter, 30 g of Raney nickel suspended in 100 ml of ethanol is added with ethanol, and catalytic reduction is carried out under ordinary temperature and ordinary pressure. When the absorption of hydrogen has cased, the supernatant is separated by decantation, and the precipitate is washed two or three times with ethanol. The supernatant and the washings are combined and concentrated under reduced pressure. The residue is dissolved in 500 ml of ethyl acetate, and the solution is washed with aqueous sodium hydrogen carbonate and filtered with 30 g of diatomaceous earth. The ethyl acetate layer is separated from the filtrate, washed with water and dried over anhydrous magnesium sulfate, and the solvent is distilled off under reduced pressure to give 24 g of N-(1-ethoxycarbonyl-3-phenylpropyl)-L-alanyl-N-(indan-2-yl)glycine tert-butyl ester as a slightly yellow, viscous oil.

IR Spectrum $\nu_{max}^{Neat}$ cm$^{-1}$: 1730(ester), 1640(amide).

NMR Spectrum (CDCl$_3$) δ: 1.27(3H,t,CH$_3$), 1.40(9H,s,CH$_3 \times 3$), 1.8–2.2(3H,m,CH$_3$), 2.6–4.5(10H,m), 3.8–3.9(2H,m,CH$_2$), 4.2(2H,q,CH$_2$), 4.9(1H,t,CH), 7.1–7.4(9H,m,Ph).

EXAMPLE 3

The N-(1-ethoxycarbonyl-3-phenylpropyl)-L-alanyl-N-(indan-2-yl)glycine tert-butyl ester obtained in Example 2 is subjected to column chromatography using 700 g of silica gel and eluted with benzene, benzene-acetone (10:1 to 4:1) and methanol-benzene (1:9) to give two fractions. Each fraction is further subjected to column chromatography using 400 g of silica gel and purified by the above procedure. The first fraction gives 2 g of N-[1-(R)-ethoxycarbonyl-3-phenylpropyl]-L-alanyl-N-(indan-2-yl)glycine tert-butyl ester as a colorless viscous oil.

$[\alpha]_D^{22} -16.4°$ (c=1, methanol).

On the other hand, the second fraction gives 16.5 g of N-[1-(S)-ethoxycarbonyl-3-phenylpropyl]-L-alanyl-N-(indan-2-yl)glycine tert-butyl ester as a colorless viscous oil.

$[\alpha]_D^{22} -12.6°$ (c=1, methanol).

EXAMPLE 4

5 g of N-[1-(S)-ethoxycarbonyl-3-phenylpropyl]-L-alanyl-N-(indan-2-yl)glycine tert-butyl ester obtained in Example 3 is dissolved in 5 ml of acetic acid, 20 ml of 25% hydrobromic acid in acetic acid is added to the solution, and the mixture is shaken for 10 minutes. The crystals which precipitate on addition of 300 ml of ethyl ether are collected by filtration to give 5 g of N-[1-(S)-ethoxycarbonyl-3-phenylpropyl]-L-alanyl-N-(indan-2-yl)glycine hydrobromide as colorless crystals melting at 180°–183° C.

$[\alpha]_D^{20} +15.6°$ (c=1.4, methanol).

EXAMPLE 5

By using N-[1-(R)-ethoxycarbonyl-3-phenylpropyl]-L-alanyl-N-(indan-2-yl)glycine tert-butyl ester obtained in Example 3 and treating as in Example 4, there can be obtained N-[1-(R)-ethoxycarbonyl-3-phenylpropyl]-L-alanyl-N-(indan-2-yl)glycine hydrobromide as colorless crystals melting at 150°–155° C.

$[\alpha]_D^{20} -20.2°$ (c=1, methanol).

EXAMPLE 6

To a mixture of 500 ml of ethyl acetate, 33 g of sodium hydrogen carbonate and 500 ml of water is added 16.2 g of N-[1-(S)-ethoxycarbonyl-3-phenylpropyl]-L-alanyl-N-(indan-2-yl)glycine hydrobromide prepared by the procedure of Example 4. After stirring to complete dissolution, the solution was adjusted to pH 4 with 1N hydrochloric acid. The ethyl acetate layer is separated, washed with water, dried and, after addition of 20 ml of 7N ethanolic hydrochloric acid, concentrated under reduced pressure. To the residue are added 250 ml of ethyl ether and 250 ml of petroleum ether, and the resulting precipitate is collected by filtration to give 11 g of N-[1-(S)-ethoxycarbonyl-3-phenylpropyl]-L-alanyl-N-(indan-2-yl)glycine hydrochloride as colorless crystals.

Recrystallization from a mixture of acetone and 1N hydrochloric acid affords colorles plates melting at 166°–170° C. with decomposition.

$[\alpha]_D^{22} +18.5°$ (c=1, methanol).

IR Spectrum $\nu_{max}^{Nujol}$ cm$^{-1}$: 1740(COOC$_2$H$_5$), 1705(COOH), 1640 (CO—N).

EXAMPLE 7

L-Alanyl-N-(indan-2-yl)glycine tert-butyl ester oxalate (4.1 g) is dissolved in 40 ml of ethanol, then 0.85 g of sodium acetate, 2 ml of acetic acid, 5 g of propyl 2-oxo-4-phenylbutyrate and 5 g of molecular sieve 3A are added, thereafter a suspension of 6 g of Raney nickel in 20 ml of ethanol is added, and catalytic reduction is carried out at ordinary temperature and ordinary pressure. When the hydrogen absorption has ceased, the supernatant is separated by decantation. The precipitate is washed two or three times with ethanol. The supernatant and the washings are combined, and the solvent is distilled off under reduced pressure. The residue is shaken with 100 ml of ethyl acetate and aqueous sodium hydrogen carbonate. Filtration with 10 g of diatomaceous earth, separation of the ethyl acetate layer of the filtrate, washing with water, drying and removal of solvent by distillation give N-(1-propoxycarbonyl-3-phenylpropyl)-L-alanyl-N-(indan-2-yl)glycine tert-butyl ester as a slightly yellow, viscous oil. To this are added 3 ml of acetic acid and 12 ml of 25% hydrobromic acid solution in acetic acid, and the mixture is shaken occasionally for 15 minutes so as to make the reaction proceed. On adding 150 ml of ethyl ether, crystalline precipitate forms, which is collected by filtration to give 3.4 g of N-(1-propoxycarbonyl-3-phenylpropyl)-L-alanyl-N-(indan-2-yl)glycine hydrobromide as colorless crystals. They are added to a mixture of 70 ml of water and 70 ml of ethyl acetate, and the mixture is stirred, neutralized with sodium hydrogen carbonate and then adjusted to pH 3-4 with 10% hydrochloric acid. The ethyl acetate layer is separated, dried over anhydrous magnesium sulfate, and made acidic with ethanolic hydrochloric acid. The solvent is distilled off, and 150 ml of ethyl ether is added to the residue. After allowing the mixture to stand for 10 minutes, the resulting crystalline precipitate is collected by filtration to give 1.7 g of N-(1-propoxycarbonyl-3-phenylpropyl)-L-alanyl-N-(indan-2-yl)glycine hydrochloride melting at 147°-150° C. with decomposition.

IR Spectrum $\nu_{max}^{Nujol}$ cm$^{-1}$: 1740(ester), 1710(COOH), 1640(CO—N).

EXAMPLE 8

The same procedure as Example 7, excepting the use of butyl 2-oxo-4-phenylbutyrate in place of propyl 2-oxo-4-phenylbutyrate, gives N-(1-butoxycarbonyl-3-phenylpropyl)-L-alanyl-N-(indan-2-yl)glycine hydrochloride melting at 154°-156° C. with decomposition.

IR Spectrum $\nu_{max}^{Nujol}$ cm$^{-1}$: 1740(ester), 1700(COOH), 1640(CO—N).

EXAMPLE 9

The same procedure as Example 7, excepting the use of isopropyl 2-oxo-4-phenylbutyrate in place of propyl 2-oxo-4-phenyl-butyrate, gives N-(1-isopropoxycarbonyl-3-phenylpropyl)-L-alanyl-N-(indan-2-yl)glycine hydrochloride melting at 150°-153° C. with decomposition.

EXAMPLE 10

The same procedure as Example 7, excepting the use of isobutyl 2-oxo-4-phenylbutyrate in place of propyl 2-oxo-4-phenylbutyrate, gives N-(1-isobutoxycarbonyl-3-phenylpropyl)-L-alanyl-N-(indan-2-yl)glycine hydrochloride melting at 148°-149° C. with decomposition.

EXAMPLE 11

The same procedure as Example 7 using methyl 2-oxo-4-phenylbutyrate in place of propyl 2-oxo-4-phenylbutyrate and methanol as the solvent in place of ethanol, gives N-(1-methoxycarbonyl-3-phenylpropyl)-L-alanyl-N-(indan-2-yl)glycine hydrochloride as colorless needles melting at 163°-165° C. with decomposition.

IR Spectrum $\nu_{max}^{Nujol}$ cm$^{-1}$: 1750(COOCH$_3$), 1705(COOH), 1640(CO—N).

EXAMPLE 12

The same procedure as Example 7, excepting the use of ethyl 4-(4-chlorophenyl)-2-oxobutyrate in place of propyl 2-oxo-4-phenylbutyrate, gives N-[1-ethoxycarbonyl-3-(4-chlorophenyl)propyl]-L-alanyl-N-(indan-2-yl)glycine hydrochloride.

Melting point 163°-168° C. (decomposition).

$[\alpha]_D^{23}$ +28.1° (c=1, methanol).

IR Spectrum $\nu_{max}^{Nujol}$ cm$^{-1}$: 1740, 1710, 1640.

EXAMPLE 13

The same procedure as Example 7, excepting the use of ethyl 2-oxo-4-(p-tolyl)butyrate in place of propyl 2-oxo-4-phenylbutyrate, gives N-[1-ethoxycarbonyl-3-(p-tolyl)propyl]-L-alanyl-N-(indan-2-yl)glycine hydrochloride.

Melting point 160°-163° C. (decomposition).

$[\alpha]_D^{23}$ +22.2° (c=1, methanol).

IR Spectrum $\nu_{max}^{Nujol}$ cm$^{-1}$: 1740, 1710, 1640.

EXAMPLE 14

To 100 ml of ethanol, there are added 3 g of L-alanyl-N-(indan-2-yl)glycine tert-butyl ester oxalate, 0.75 g of sodium acetate, 1.5 g of acetic acid, 5 g of molecular sieve 3A and 5 g of ethyl 4-(4-benzyloxyphenyl)-2-oxobutyrate, and catalytic reduction is carried out using Raney nickel as catalyst. When the hydrogen absorption has ceased, the catalyst is removed, and catalytic reduction is further carried out using palladium-carbon as catalyst. The catalyst is filtered off and the solvent is distilled off under reduced pressure to give N-[1-ethoxycarbonyl-3-(p-hydroxyphenyl)propyl]-L-alanyl-N-(indan-2-yl)glycine tert-butyl ester as oil. This oil is converted by the reaction procedure as used in Example 4 to N-[1-ethoxycarbonyl-3-(4-hydroxyphenyl)propyl]-L-alanyl-N-(indan-2-yl)glycine hydrobromide, which is further converted to the hydrochloride by the procedure of Example 6. There is thus obtained 0.65 g of N-[1-ethoxycarbonyl-3-(4-hydroxyphenyl)propyl]-L-alanyl-N-(indan-2-yl)glycine hydrochloride as colorless crystals melting at 126°-130° C. with decomposition.

$[\alpha]_D^{24}$ +17.7° (c=1, methanol).

Mass Spectrum m/e: 450(M$^+$—HCl—H$_2$O), 335, 334, 331, 330, 284, 215, 214, 169, 168, 133, 129, 120, 117, 116, 107.

EXAMPLE 15

L-Alanyl-N-(indan-2-yl)glycine (3.5 g) is suspended in a mixture of 30 ml of ethanol and 20 ml of water, and to the suspension is added 15 g of ethyl 2-oxo-4-(3,4-dimethoxyphenyl)butyrate. With stirring at room temperature, a solution of 1.4 g of sodium cyanoborohydride in 10 ml of ethanol is added dropwise over about 3 hours. After stirring for an hour, the reaction mixture is concentrated, water is added, and the insoluble matter is removed by extraction with ether. On adjusting the aqueous layer to pH 4 with diluted hydrochloric acid, an oil separates, which is extracted with ethyl acetate. The ethyl acetate layer is washed with water, dried and concentrated under reduced pressure. On adding first 2 ml of 4N hydrochloric acid-ethanol solution and then 300 ml of ether to the residue, an oily substance separates. The ether is removed by decantation, and the oil is further washed with ether by the same procedure, whereby the oil turns into powder. This powder is crystallized by treatment with dichloromethane-ether and recrystallized from the same mixed solvent to give 0.4 g of N-[1-(S)-ethoxycarbonyl-3-(3,4-dimethoxyphenyl)propyl]-L-alanyl-N-(indan-2-yl)glycine hydrochloride as crystals melting at 138°–140° C. with decomposition.

$[\alpha]_D^{22}+34°$ (c=0.5, ethanol).

EXAMPLE 16

L-Alanyl-N-(indan-2-yl)glycine (1.0 g) and 6.0 g of phenylpyruvic acid are dissolved in 50 ml of 70% aqueous methanol, and the pH is adjusted to 7.0 with aqueous potassium hydroxide. Sodium cyanoborohydride (1.0 g) is added to this solution. After allowing the mixture to stand at room temperature overnight, the solvent is distilled off under reduced pressure, the residue is dissolved in 2 ml of water, made adsorbed on a Dowex 50 (H+) [trade name of ion-exchange resin] column and eluted with 2% pyridine. The solvent is distilled off under reduced pressure, the residue is purified by silica gel column chromatography using acetonitrile-methanol (4:1) as the developer to give 0.3 g of N-(1-carboxy-2-phenylethyl)-L-alanyl-N-(indan-2-yl)glycine as colorless powder.

Elemental Analysis for $C_{23}H_{26}N_2O_5 \cdot HCl$: Calcd.: C, 61.81; H, 6.09; N, 6.27. Found: C, 61.43; H, 6.08; N, 6.61.

NMR Spectrum (D$_2$O) δ: 1.20–1.60(3H,CH$_3$), 2.80–4.02(10H), 4.90–5.30(1H), 7.10–8.40(10H,Ph)

Mass Spectrum m/e: 392(M—H$_2$O).

EXAMPLE 17

By using 1.0 g of L-alanyl-N-(indan-2-yl)glycine, 6.0 g of 2-oxo-butyric acid and 1.0 g of sodium cyanoborohydride in a similar procedure to that of Example 1, there can be obtained 0.4 g of N-(1-carboxypropyl)-L-alanyl-N-(indan-2-yl)glycine as colorless powder.

Elemental analysis for $C_{18}H_{24}N_2O_5$: Calcd. C, 62.05; H, 6.94; N, 8.04. Found: C, 61.97; H, 7.58; N, 7.46.

NMR Spectrum (D$_2$O) δ: 1.00(3H,J=6 Hz,CH$_3$), 1.25–1.50(3H, —CH$_3$), 3.00–3.85(10H), 5.10–5.20(1H), 7.28(4H,Ph)

Mass spectrum m/e: 330(M—H$_2$O).

EXAMPLE 18

N-(N′-Ethoxycarbonylmethyl-N′-benzylglycycl)-N-(indan-2-yl)glycine benzyl ester (3 g) is dissolved in 100 ml of ethanol, and catalytic reduction is carried out at ordinary temperature and pressure using 5% palladium-carbon as catalyst. After absorption of 2 equivalents of hydrogen, the reaction mixture is filtered to remove the catalyst. The ethanol is distilled off under reduced pressure to give an oily substance. Addition of ethanolic hydrochloric acid with 100 ml of ether to the oily substance gives N-(N′-ethoxycarbonylmethylglycycl)-N-(indan-2-yl)glycine hydrochloride as colorless powder.

Elemental analysis for $C_{17}H_{22}N_2O_5 \cdot HCl \cdot \frac{1}{2}H_2O$: Calcd.: C, 53.75; H, 6.37; N, 7.38. Found: C, 53.63; H, 6.87; N, 7.18.

Mass Spectrum m/e: 316(M—3/2H$_2$O—HCl)

EXAMPLE 19

N-(1-(S)-Ethoxycarbonyl-3-phenylpropyl)-L-alanyl-N-(indan-2-yl)glycine hydrochloride (1.2 g) is dissolved in 30 ml of methanol. To the solution is added 5 ml of 2N aqueous sodium hydroxide. After stirring at room temperature overnight, the reaction mixture is concentrated under reduced pressure, and 30 ml of water is added. On adjusting the pH to 5–6 with diluted hydrochloric acid, an oil separates, which is extracted with ethyl acetate. The ethyl acetate layer is washed with water and dried, and the solvent is distilled off under reduced pressure. Methanol (5 ml) is added to the residue, and the solution is allowed to stand. There is obtained 0.6 g of N-(1-(S)-carboxyl-3-phenylpropyl)-L-alanyl-N-(indan-2-yl)glycine as crystals melting at 140°–142° C.

$[\alpha]_D^{22}+26°$ (c=0.6, 1% HCl).

EXAMPLE 20

N-[1-Ethoxycarbonyl-3-(3,4-dimethoxyphenyl)-propyl]-L-alanyl-N-(indan-2-yl)glycine hydrochloride (1.1 g) is dissolved in 30 ml of methanol. To the solution is added 5 ml of 2N aqueous sodium hydroxide. After stirring for 4 hours, the reaction mixture is concentrated, and 30 ml of water is added. On adjusting the pH to about 5 with diluted hydrochloric acid, an oily substance separates, which is extracted with ethyl acetate. The extract is washed with water, dried and concentrated. Methanol (4 ml) is added to the residue, and the mixture is allowed to stand. There is obtained 60 mg of N-[1-carboxy-3-(3,4-dimethoxyphenyl)propyl]-L-alanyl-N-(indan-2-yl)glycine as crystals melting at 160°–165° C. with decomposition.

EXAMPLE 21

L-Leucyl-N-(indan-2-yl)glycine tert-butyl ester (3.5 g) is dissolved in 50 ml of ethanol, and 3.5 g of ethyl 2-oxo-4-phenylbutyrate, 1.5 g of sodium acetate, 3.5 g of acetic acid, 7.0 g of molecular sieve 3A and 5.0 g of Raney nickel are added, and catalytic reduction is carried out under ordinary temperature and pressure. After absorption of the theoretical amount of hydrogen, the catalyst is filtered off, and the filtrate is concentrated under reduced pressure. To the residue, 100 ml of water and 2 g of sodium hydrogen carbonate are added, and the mixture is extracted with 200 ml of ethyl acetate. After washing the extract with water and drying, the ethyl acetate is distilled off under reduced pressure, and 20 ml of acetic acid and 5 ml of 25% hydrobromic acid solution in acetic acid are added to the residue. After stirring at room temperature for 10 minutes, 100 ml of ether is added, and the resulting oil layer is separated and washed with ethyl ether to give N-(1-ethoxycarbonyl-3-phenylpropyl)-L-leucyl-N-(indan-2-yl)glycine hydrobromide. This is suspended in 10 ml of water, the suspension is made alkaline with sodium hydrogen carbonate, and the insoluble matter is extracted with ethyl ether. The aqueous layer is adjusted to pH 4.0 with 10% hydrochloric acid, and extracted with 200 ml of ethyl acetate. The extract is washed with water and dried over magnesium sulfate, 1 ml of ethanolic hydrochloric acid is added, and the ethyl acetate is distilled off under reduced pressure. On adding 200 ml of ethyl ether to the residue and allowing the mixture to stand at room temperature, there is yielded 0.8 g of N-(1-ethoxycarbonyl- 3-phenylpropyl)-L-leucyl-N-(indan-2-yl)glycine hydrochloride as colorless amorphous powder.

NMR Specerum (d<sub>6</sub>-DMSO) δ: 0.93(6H,d,J=3 Hz,CH(CH<sub>3</sub>)<sub>2</sub>), 1.30(3H,t,J=7 Hz,CH<sub>3</sub>), 2.90–3.20(4H,m,CH<sub>2</sub>), 3.90(2H,s,CH<sub>2</sub>), 4.00–4.35(3H,m), 7.20(4H,s,Ph), 7.30(5H,s,Ph)

Mass Spectrum m/e: 476, 431, 361, 315, 171.

EXAMPLE 22

N<sup>ε</sup>-carbobenzoxy-L-lysyl-N-(indan-2-yl)glycine tert-butyl ester oxalate (3.5 g) is dissolved in 20 ml of methanol, and 1 g of sodium acetate, 1.2 g of acetic acid, 8 g of molecular sieve and 15 g of ethyl 2-oxo-4-phenylbutyrate are added. To this mixture is added dropwise with stirring a solution of 3.3 g of sodium cyanoborohydride in 30 ml of methanol over 2 hours. 3 g of sodium cyanoborohydride is further added, and the mixture is stirred for 3 hours. After addition of 200 ml of 25% aqueous phosphoric acid, the reaction mixture is extracted with two 200-ml portions of ethyl acetate. The extract is washed with 0.5N aqueous sodium hydroxide and with water, and dried over anhydrous magnesium sulfate. The ethyl acetate is distilled off under reduced pressure, and the oil thus obtaned is separated and purified by silica gel column chromatography (acetone-benzene (1:12 to 1:5)). The first fraction gives 1.1 g of N<sup>α</sup>-[1-(R)-ethoxycarbonyl-3-phenylpropyl]-N<sup>ε</sup>-carbobenzoxy-L-lysyl-N-(indan-2-yl)glycine tert-butyl ester as an oil.

Elemental analysis for C<sub>41</sub>H<sub>53</sub>N<sub>3</sub>O<sub>7</sub>: Calcd.: C, 70.36; H, 7.63; N, 6.00. Found: C, 69.89; H, 7.64; N, 5.76.

[α]<sub>D</sub><sup>24</sup>= −4.5° (c=1, methanol).

The second fraction gives 1 g of N<sup>α</sup>-[1-(S)-ethoxycarbonyl-3-phenylpropyl]-N<sup>ε</sup>-carbobenzoxy-L-lysyl-N-(indan-2-yl)glycine tert-butyl ester as an oil.

Elemental analysis for C<sub>41</sub>H<sub>53</sub>N<sub>3</sub>O<sub>7</sub>: Calcd.: C, 70.36; H, 7.63; N, 6.00. Found: C, 70.28; H, 7.51; N, 5.93.

[α]<sub>D</sub><sup>24</sup>= −8.2° (c=1, methanol).

IR Spectrum ν<sub>max</sub><sup>neat</sup>cm<sup>−1</sup>: 3300(NH), 1720(C=O), 1630(C=O).

EXAMPLE 23

N<sup>α</sup>-[1-(R)-Ethoxycarbonyl-3-phenylpropyl]-N<sup>ε</sup>-carbobenzoxy-L-lysyl-N-(indan-2-yl)glycine tert-butyl ester (1 g) is dissolved in 2 ml of acetic acid. To the solution, 8 ml of 25% hydrobromic acid solution in acetic acid is added, and the mixture is allowed to stand at room temperature for 30 minutes. On adding 200 ml of ether and 100 ml of petroleum ether to the reaction mixture, a crystalline precipitate forms. This is collected by filtration and recrystallized from a mixture of methanol and ethyl ether to give 0.8 g of N<sup>α</sup>-[1-(R)-ethoxycarbonyl-3-phenylpropyl]-L-lysyl-N-(indan-2-yl)glycine dihydrobromide melting at 128°–133° C. with decomposition.

[α]<sub>D</sub><sup>24</sup>= −11.6° (c=1, methanol).

EXAMPLE 24

By a procedure similar to that described in Example 23, there is obtained 0.6 g of N<sup>α</sup>-[1-(S)-ethoxycarbonyl-3-phenylpropyl]-L-lysyl-N-(indan-2-yl)glycine dihydrobromide from 0.9 g of N<sup>α</sup>-[1-(S)-ethoxycarbonyl-3-phenylpropyl]-N<sup>ε</sup>-carbobenzoxy-L-lysyl-N-(indan-2-yl)glycine tert-butyl ester. Melting point: 160°–165° C. (decomposition)

[α]<sub>D</sub><sup>24</sup>+18.0° (c=1, methanol).

EXAMPLE 25

By reacting L-alanyl-N-(indan-2-yl)glycine tert-butyl ester oxalate (2.0 g) with N-butyl-2-oxo-4-phenylbutyrylamide (4.0 g) in a similar manner to that of Example 2, there is obtained N-(1-butylaminocarbonyl-3-phenylpropyl)-L-alanyl-N-(indan-2-yl)glycine tert-butyl ester (0.5 g) as colorless oil.

NMR Spectrum (CDCl<sub>3</sub>): 1.90(3H,m,CH<sub>3</sub>), 1.40–1.55(16H,m), 2.60–3.49(8H,m,CH<sub>2</sub>), 3.70–3.95(2H,m), 7.20(4H,s,Ph), 7.30(5H,s,Ph).

EXAMPLE 26

Use of N-(1-butylaminocarbonyl-3-phenylpropyl)-L-alanyl-N-(indan-2-yl)glycine tert-butyl ester (0.5 g) as a reactant in a similar manner to that of Example 4, gives N-(1-butylaminocarbonyl-3-phenylpropyl)-L-alanyl-N-(indan-2-yl)glycine hydrobromide as colorless amorphous powder.

NMR Spectrum (d<sup>6</sup>-DMSO) δ: 0.8–1.0(3H,m,CH<sub>3</sub>), 1.2–1.55 (7H,m,CH<sub>3</sub>+CH<sub>2</sub>×2), 1.90–2.25(2H,m,CH<sub>2</sub>), 2.40–2.60(2H,m,CH<sub>2</sub>), 2.95–3.30(6H,m,CH<sub>2</sub>), 4.80–5.0(1H,m,CH), 7.10–7.30(9H,m,Ph).

EXAMPLE 27

L-Alanyl-N-(indan-2-yl)-β-alanine (2.0 g) is dissolved in a mixture of 20 ml of water and 100 ml of ethanol, 10 g of ethyl 2-oxo-4-phenylbutyrate is added, and a solution of 0.94 g of sodium cyanoborohydride in 20 ml of ethanol is added dropwise over 2 hours. The mixture is stirred at room temperature for 3 hours and then adjusted to pH 4.0 with 10% hydrochloric acid, and the ethanol is distilled off under reduced pressure. The residue is extracted with 200 ml of ethyl acetate, washed with water and dried, and the ethyl acetate is distilled off under reduced pressure. The residue is dissolved in 2 ml of 20% ethanolic hydrochloric acid, 100 ml of ethyl ether is added, and the mixture is allowed to stand at room temperature. Thus is obtained 1.2 g of N-(1-ethoxycarbonyl-3-phenylpropyl)-L-alanyl-N-(indan-2-yl)-β-alanine hydrochloride as colorless amorphous powder.

NMR Spectrum (d<sub>6</sub>-DMSO) δ: 1.30(3H,t,J=7.5 Hz), 1.40(3H,d,J=4.5 Hz), 2.65–3.00(4H,m,CH<sub>2</sub>), 3.20–3.40(4H,m,CH<sub>2</sub>), 4.25(2H,q,J=7.5 Hz,CH<sub>2</sub>), 7.20(4H,s,Ph), 7.30(5H,s,Ph).

EXAMPLE 28

L-Alanyl-N-(1,2,3,4-tetrahydrophthalen-2-yl)glycine (3.0 g) is dissolved in 200 ml of ethanol, 15 g of ethyl 2-oxo-4-phenylbutyrate and 12 g of molecular sieve 3A are added, and the mixture is stirred at room temperature for 30 minutes. Thereafter, a solution of 1.3 g of sodium cyanoborohydride in 50 ml of ethanol is added dropwise over 6 hours, and stirring is further continued for 2 hours. The insoluble matter is filtered off, and the filtrate is concentrated to dryness under reduced pressure. Water (50 ml) is added to the residue, the mixture is made alkaline with sodium hydrogen carbonate, and the insoluble matter is removed by extraction with ethyl ether. The aqueous layer is adjusted to pH 4.0 with 10% hydrochloric acid and then extracted with 200 ml of ethyl acetate. The extract is washed with water and dried, 1 ml of 20% alcoholic hydrochloric acid is added, and the ethyl acetate is distilled off under reduced pressure. Ethyl ether (100 ml) is added to the residue, and the mixture is allowed to stand at room temperature to give 1.5 g of N-(1-ethoxycarbonyl-3-phenylpropyl)-L- alanyl-N-(1,2,3,4-tetrahydronaphthalen-2-yl)glycine hydrochloride as colorless amorphous powder.

NMR Spectrum (d$_6$-DMSO) δ: 1.30(3H,t,J=7 Hz,CH$_3$), 1.40 (3H,d,J=6 Hz,CH$_3$), 1.70–2.30(5H,m,CH$_2$), 2.80–3.05(7H,m,CH$_2$), 4.00(2H,s,CH$_2$), 4.30(2H,q,J=7 Hz,CH$_2$), 7.10 (4H,s,Ph), 7.30(5H,s,Ph).

Mass Spectrum m/e: 448(M—HCl—H$_2$O), 344, 319, 168.

EXAMPLE 29

By reacting 3 g of L-alanyl-N-(indan-1-yl)glycine with 15 g of ethyl 2-oxo-4-phenylbutylate and treating the reaction mixture as in Example 28, there is obtained 1.2 g of N-(1-ethoxycarbonyl-3-phenylpropyl]-L-alanyl-N-(indan-1-yl)glycine hydrochloride as colorless amorphous powder.

NMR Spectrum (d$_6$-DMSO) δ: 1.20–1.45(3H,m,CH$_3$), 1.55–1.65(3H,m,CH$_3$), 2.70–3.05(4H,m,CH$_2$), 4.00(2H,s,CH$_2$), 4.40(2H,q,J=7 Hz,CH$_2$), 4.80–5.00(1H,m,

7.30(9H,s,Ph).

Mass Spectrum m/e: 434(M—HCl—H$_2$O), 258, 244, 180.

EXAMPLE 30

By reacting 3 g of L-alanyl-N-(5-hydroxyindan-1-yl)glycine with 15 g of ethyl 2-oxo-4-phenylbutylate and treating the reaction mixture as in Example 28, there is obtained 0.8 g of N-(1-ethoxycarbonyl-3-phenylpropyl)-L-alanyl-N-(5-hydroxyindan-1-yl)glycine hydrochloride as colorless amorphous powder.

NMR Spectrum (d$^6$-DMSO) δ: 1.10–1.70(6H,m,CH$_3$×2), 1.75–3.30(8H,m,CH$_2$×4), 3.70–4.30(5H,m,CH$_2$×2+CH), 4.60–5.20(2H,m,CH×2), 6.55–7.30(8H,m,Ph).

EXAMPLE 31

L-Alanyl-N-(5,6-dimethoxyindan-1-yl)glycine tert-butyl ester (4.0 g) is dissolved in 80 ml of ethanol, and 0.77 g of sodium acetate, 4.0 g of acetic acid, 4.0 g of ethyl 2-oxo-4-phenyl-butyrate, 12 g of molecular sieve 3A and 6.0 g of Raney nickel are added. Thereafter, the reaction and treatment are carried out as in Example 2 to give 2.0 g of N-(1-ethoxycarbonyl-3-phenylpropyl)-L-alanyl-N-(5,6-dimethoxyindan-1-yl)glycine tert-butyl ester as slightly yellow oil.

NMR Spectrum (CDCl$_3$) δ: 1.20–1.50(15H,m,CH$_3$×5), 1.90–2.20(2H,m,CH$_2$), 2.50(2H,s,CH$_2$), 2.60–2.95(4H,m,CH$_2$), 3.80(3H,s,OCH$_3$), 3.90(3H,s,OCH$_3$), 4.20(2H,q,J=7.0 Hz,CH$_2$), 5.40–5.60(1H,m,CH), 6.80–6.90(2H,m,Ph), 7.25 (5H,s,Ph).

Mass Spectrum m/e=568(M+), 495, 361, 308, 234.

EXAMPLE 32

N-(1-Ethoxycarbonyl-3-phenylpropyl)-L-alanyl-N-(5,6-dimethoxyindan-1-yl)glycine tert-butyl ester (2.0 g) is dissolved in 10 ml of acetic acid, and 2 ml of 25% hydrobromic acid in acetic acid is added dropwise with ice cooling. After allowing the mixture to stand at room temperature for 5 minutes, 50 ml of ethyl ether is added to the reaction mixture, whereupon amorphous powder precipitates. This is collected by filtration and dissolved in 10 ml of water. The solution is made alkaline with sodium hydrogen carbonate, and the insoluble matter is removed by extraction with ethyl ether. The aqueous layer is adjusted to pH 4.0 with 10% hydrochloric acid and extracted with 100 ml of chloroform. The extract is washed with water and dried, 1 ml of 20% ethanolic hydrochloric acid is added, and the chloroform is distilled off under reduced pressure. The residue is dissolved in 2 ml of ethanol. On adding 20 ml of ethyl ether, colorless amorphous powder precipitates. Collection of this precipitate by filtration gives 0.2 g of N-(1-ethoxycarbonyl-3-phenylpropyl)-L-alanyl-N-(5,6-dimethoxy-indan-1-yl)glycine hydrochloride as colorless powder.

NMR Spectrum (d$_6$-DMSO) δ: 1.25(3H,t,J=8 Hz,CH$_3$), 1.40 (3H, d, J=4.5 Hz,CH$_3$), 3.75 (3H,s,OCH$_3$), 3.80(3H,s,OCH$_3$), 6.80(1H,s,Ph), 6.90(1H,s,Ph), 7.25(5H,s,Ph).

EXAMPLE 33

By the similar procedure to that in Example 32, N-(1-ethoxycarbonyl-3-phenylpropyl)glycyl-N-(indan-2-yl)glycine hydrochloride is obtained from N-(1-ethoxycarbonyl-3-phenylpropyl)glycyl-N-(indan-2-yl)glycine tert-butyl ester as colorless amorphous powder.

NMR Spectrum (d$^6$-DMSO) δ: 1.30(3H,t,J=6 Hz,CH$_3$), 2.25(2H,m,CH$_2$), 2.70(2H,m,CH$_2$), 2.90–3.20(4H,m,CH$_2$), 4.00–4.60(5H,m), 4.80–5.10(1H,m), 7.30(4H,s), 7.35(5H,s,Ph).

EXPERIMENT 1

Inhibitions of Angiotensin I Converting Enzyme (ACE) by the Compounds of this Invention.

EXPERIMENTAL METHOD

The experiment was conducted in accordance with a modification of the method described by Cushman et al. [Biochemical Pharmacology, Vol. 20, 1637(1971)]. That is, using hippuryl-L-histidyl-L-leucine(HHL) as the substrate, the ACE inhibitory activity was determined in terms of percent inhibition on the amount of hippuric acid produced by ACE when the present compound was added. A solution of the compound of the present invention dissolved in a 0.02 to 2% dimethyl sulfoxide-100 mM potassium phosphate buffer solution (pH 8.3, containing 300 mM sodium chloride) was added to 100 μl of ACE (protein concentration, 20 mg/ml) and 100 μl of 1.25 mM HHL. In this experiment, a potassium phosphate buffer solution containing dimethyl sulfoxide at a concentration equal to that of the test solution was used as a control. After incubating the solution at 37° C. for one hour, 150 μl of 1N hydrochloric acid was added to the solution to terminate the reaction. After 1 ml of ethyl acetate was added, the solution was centrifuged at 3000 r.p.m. for 10 minutes. A 0.5 ml aliquot was separated from the ethyl acetate layer and dried at a temperature below 50° C. under nitrogen gas streams. The residue was mixed with 5 ml of 1M aqueous sodium chloride and the mixture was subjected to colorimetry at a wavelength of 228 nm.

TEST RESULT

The test results obtained with respect to the compounds of Examples 1, 7, 8, 9 and 19 are shown in Table 2 below.

TABLE 2

| Example No. of Tested Compound | Concentration ($\mu$M) | Inhibitory Activity on ACE (%) |
|---|---|---|
| 1 | 1 | 87 |
|   | 10 | 97 |
| 7 | 1 | 91 |
|   | 10 | 97 |
| 8 | 1 | 69 |
|   | 10 | 99 |
| 9 | 1 | 72 |
|   | 10 | 95 |
| 19 | 1 | 95 |
|   | 10 | 98 |

EXPERIMENT 2

Effect of Present Compounds against Hypertensive Activity of Angiotensin I

EXPERIMENTAL METHOD

Male rats (Sprague-Dawley) weighing 250 g to 350 g which were fed under free access to drinking water and feeds were used as experimental animals. The rats were anesthetized with intraperitoneal administration of pentobarbital sodium (50 mg/kg) on the day before the test day and a polyethylene tube was inserted into each of the femoral artery for measurement of blood pressure and the femoral vein for injection of angiotensin I and II, and then the tubes were fixed.

On the test day, an average blood pressure in the control phase was recorded on an electric hemodynamometer (MP-4T model manufactured by Nippon Koden, Japan) and thereafter angiotensin I and then angiotensin II were injected through the femoral vein at a dose of 300 ng/kg and 100 ng/kg respectively, to measure the hypertensive activity. Then, 13.8 $\mu$M/kg of the compound of this invention was administered orally as an aqueous solution or an aqueous gum arabic suspension, and 20, 60 and 120 minutes after the administration, angiotensin I and II were injected repeatedly to trace hypertensive reactions. In calculating the percent inhibition to the hypertensive activity of angiotensin I, the percent inhibitory value was corrected based on the variation with time in the hypertensive reaction by angiotensin II.

TEST RESULT

The test results obtained with respect to the compounds of Examples 1, 7, 9 and 15 are shown in Table 3 below.

TABLE 3

| Example No. of Tested Compound | Percent Inhibition (%) against Hypertensive Reaction by Angiotensin I | | |
|---|---|---|---|
|   | After 20 min. | After 60 min. | After 120 min. |
| 1 | 93 | 88 | 77 |
| 7 | 84 | 91 | 96 |
| 9 | 88 | 71 | 51 |
| 15 | 84 | 80 | 65 |

PREPARATION EXAMPLE

The compounds (I) of the present invention are used, for example, for the treatment of hypertension in the following examples of formulation.

1. Tablets

| | |
|---|---|
| (1) N—(1-Ethoxycarbonyl-3-phenylpropyl)-L-alanyl-N—(indan-2-yl)glycine hydrochloride | 10 g |
| (2) Lactose | 90 g |
| (3) Corn Starch | 29 g |
| (4) Magnesium Stearate | 1 g |
| | 130 g for 1000 tablets |

The above ingredients (1), (2) and 17 g of corn starch are blended, and granulated using a paste prepared from 7 g of corn starch. Five grams of corn starch and the ingredient (4) are added to the resulting granules and the mixture is compressed by a tabletting machine to prepare 1000 tablets having a diameter 7 mm each containing 10 mg of the active ingredient (1).

2. Capsules

| | |
|---|---|
| (1) N—(1-Butoxycarbonyl-2-phenylethyl)-L-alanyl-N—(indan-2-yl)glycine hydrochloride | 10 g |
| (2) Lactose | 135 g |
| (3) Cellulose Fine Powder | 70 g |
| (4) Magnesium Stearate | 5 g |
| | 220 g for 1000 capsules |

All of the above components are blended and encapsulated into Gelatin Capsule No. 3 (IX Japanese Pharmacopoiea) to prepare 1000 capsules each containing 10 mg of the active component (1).

3. Injectable Solution

| | |
|---|---|
| (1) N—[1-(S)-Carboxy-3-phenylpropyl)-L-alanyl-N—(indan-2-yl)glycine sodium salt | 10 g |
| (2) Sodium Chloride | 9 g |
| (3) Chlorobutanol | 5 g |
| (4) Sodium Bicarbonate | 1 g |

All of the above ingredients are dissolved in 1000 ml of distilled water and charged into 1000 brown ampules each containing 1 ml of the solution. The ampules are replaced with nitrogen gas and sealed. The entire preparation steps are conducted under sterile conditions.

What is claimed is:

1. L-alanyl-N-(indan-2-yl)glycine or a $C_{1-4}$-alkyl ester or salt thereof.

2. L-alanyl-N-(indan-2-yl)glycine.

3. A $C_{1-4}$-alkyl ester of L-alanyl-N-(indan-2-yl)glycine according to claim 1.

4. L-alanyl-N-(indan-2-yl)glycine tert-butyl ester.

5. A compound according to claim 1 in the form of an acid addition salt.

6. L-alanyl-N-(indan-2-yl)glycine tert-butyl ester oxalate.

* * * * *